United States Patent [19]

Ho et al.

[11] Patent Number: 4,908,384

[45] Date of Patent: Mar. 13, 1990

[54] FATTY ACID LEUKOTRIENE SYNTHESIS INHIBITORS

[75] Inventors: Chih Y. Ho, Lansdale; Richard J. Mohrbacher, Maple Glen, both of Pa.

[73] Assignee: McNeilab, Inc., Spring House, Pa.

[21] Appl. No.: 902,366

[22] Filed: Aug. 29, 1986

[51] Int. Cl.$^4$ .................. A61K 71/19; A61K 13/165; A61K 31/215; C07C 59/40

[52] U.S. Cl. .................... 514/559; 260/413; 514/558; 514/560; 562/621

[58] Field of Search ............. 514/558, 559, 560; 260/500.5 H, 413 Q

[56] References Cited

U.S. PATENT DOCUMENTS

| | | | |
|---|---|---|---|
| 2,178,760 | 11/1939 | Lazier | 260/413 Q |
| 2,227,823 | 1/1941 | Cox | 260/413 Q |
| 3,057,893 | 10/1962 | Smith et al. | 260/413 Q |
| 3,741,204 | 6/1973 | Thiele | 514/558 |
| 4,497,827 | 2/1985 | Nelson | 260/500.5 H |
| 4,564,476 | 1/1986 | Ho | 260/404 |

FOREIGN PATENT DOCUMENTS 150038  11/1981  Japan ................... 514/560

OTHER PUBLICATIONS

The Merck Index, 10th ed., (1983), p. 265, 1186 and 1187.
Tetrahedron Letters, vol. 24, No. 46, pp. 5139–5140, 1983, "Synthesis and 5-Lipoxygenase...", Ackroyd et al.
"Trace Constituents in Milk Fat:...", Weihrauch et al., Lipids 9(11):883–890 (1974).
"Synthesis of 4-4 Monohydroxyhexadecanoic Acids", Aliphatics, vol. 99, 1983, 99:21917p, pp. 569–570, Ozeris.
Chemical Abstracts, "Synthesis of Aryl and Arylalkyl Keto Acids by Oxidation with Chromium Trioxide", vol. 81, 1974, 151744u, Oyman.
"Metabolism of Hydroxy Fatty Acdis", The J. of Biochem., vol. 54, No. 6, 1963, Seiichi Okui et al., pp. 536–540.
"Metabolism of Hydroxy Fatty Acids", The J. of Biochem., vol. 58, No. 2, 1965, Michinao Mizugaki et al., pp. 174–178.

*Primary Examiner*—J. E. Evans

[57] ABSTRACT

Fatty acid compounds of the formula (I):

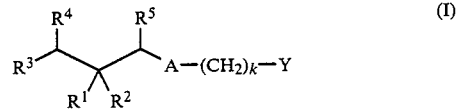

(I)

wherein $R^1$, $R^2$, $R^3$, $R^4$, $R^5$, A, Y and k are as defined herein are novel and useful in the treatment of allergic and inflammatory disorders.

20 Claims, No Drawings

FATTY ACID LEUKOTRIENE SYNTHESIS INHIBITORS

BACKGROUND OF THE INVENTION

The metabolism of arachidonic acid via the lipoxygenase pathway gives rise to leukotrienes which are potent mediators of inflammation and allergic reactions. Compounds which block the generation, release or action of leukotrienes to alleviate inflammation and allergic reactions are described in U.S. Pat. No. 4,564,476 issued Jan. 14, 1986 and in Science, Vol. 215, pages 1380–1383 (Mar. 12, 1982).

SUMMARY OF THE INVENTION

Fatty acid derivatives defined by the following formula (I):

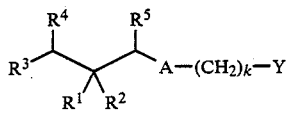

wherein $R^1$, $R^2$, $R^3$, $R^4$, $R^5$, A, Y and k are as defined herein are novel and useful in the treatment of certain inflammatory and allergic disorders in mammlas, e.g. humans, such as asthma and other chronic obstructive pulmonary diseases, arthritis, psoriasis, chronic colitis and myocardial infarction.

DETAILED DESCRIPTION OF THE INVENTION

The compounds of the present invention are of the following formula (I):

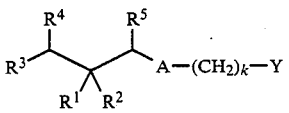

wherein
A is —CH$_2$—, alkylidene, 1-alkylalkylidene, —CR$^6$=CR$^7$—, or —C≡C—;
Y is —COOH, alkoxycarbonyl, carboxamido (—CONH$_2$), N-hydroxycarboxamido (—CONHOH), N-alkylcarboxamido or N,N-dialkylcarboxamido;
$R^1$ is hydroxy, mercapto, acetoxy, acetylthio, alkoxy, alkylthio or halo;
$R^2$ is hydrogen or $R^1$ and $R^2$ taken together are carbonyl, —O(CH$_2$)$_2$O— or —O(CH$_2$)$_3$O—;
$R^3$ is alkyl of at least 6 carbons, alkoxy, —O—(CH$_2$)$_m$—alkaryl, —O—(CH$_2$)$_m$—alkoxyaryl, —(CH$_2$)$_n$—aryl, —(CH$_2$)$_n$—alkaryl or —(CH$_2$)$_n$—alkoxyaryl;
$R^4$ is hydrogen or alkyl;
$R^5$ is hydrogen or alkyl;
$R^6$ is hydrogen or alkyl;
$R^7$ is hydrogen or alkyl;
k is the integer 2–7;
m is the integer 0–4;
n is the integer 1–6; and
when Y is —COOH, the pharmaceutically-acceptable base addition salts thereof, provided that if A is —CH$_2$—, alkylidene or 1-alkylalkylidene, $R^3$ is not alkyl or —(CH$_2$)$_n$aryl.

A, in more detail, is methylene of the formula —CH$_2$—; alkylidene of about 2 to 4 carbons such as ethylidene (—CH(CH$_3$)—), propylidene or 2-methylpropylidene; 1-alkylalkylidene of about 1 to 3 carbons in such alkyl and about 2 to 4 carbons in the alkylidene such as 1-methylpropylidene, 1-propylpropylidene or 1-methylbutylidene; unsubstituted or substituted ethenylene of the formula —CR$^6$=CR$^7$— wherein $R^6$ and $R^7$ may be cis or trans to each other; or ethynylene of the formula —C≡C—. A particular A is —CR$^6$=CR$^7$—, wherein $R^6$ and $R^7$ are both hydrogen and are cis to each other.

Y, in more detail, is —COOH; alkoxycarbonyl wherein the alkoxy moiety is of about 1 to 4 carbons such as methoxycarbonyl, ethoxycarbonyl or propoxycarbonyl, carboxamido (—CONH$_2$); N-hydroxycarboxamido; N-alkylcarboxamido, e.g. wherein the alkyl is of about 1 to 4 carbons such as methyl, ethyl, n-propyl, iso-propyl or sec-butyl; and N,N-dialkylcarboxamido, e.g. wherein each alkyl is independently of about 1 to 4 carbons, e.g. methyl or tert-butyl. A particular Y is —COOH.

$R^1$, in more detail, is hydroxy; mercapto; acetoxy; acetylthio; alkoxy of about 1 to 4 carbons such as methoxy, ethoxy or tert-butoxy; alkylthio of about 1 to 4 carbons such as methylthio, ethylthio or n-butylthio; or halo such as fluoro, chloro, bromo or iodo. $R^1$ is particularly hydroxy.

$R^2$, in more detail, is hydrogen or $R^1$ and $R^2$ taken together is carbonyl or a ketal of the formula —O(CH$_2$)$_2$O— or —O(CH$_2$)$_3$O—.

$R^3$, in more detail, is straight or branched chain alkyl of about 6 to 15 carbons, in particular 8 to 15 carbons and preferably straight chain alkyl such as n-hexyl, 2-methylhexyl, 2,2-dimethyldodecyl, n-octyl or n-pentadecyl; alkoxy of about 6 to 15 carbons such as n-hexoxy, 2-methyloctoxy or 4,5-dimethyltridecoxy; —O—(CH$_2$)$_m$-alkaryl, e.g. wherein the alkyl moiety of said alkaryl is alkyl of about 1 to 8 carbons such as methyl, n-pentyl or iso-octyl and the aryl moiety is phenyl; —O—(CH$_2$)$_m$-alkoxyaryl wherein the alkoxy moiety of said alkoxyaryl is alkoxy of about 1 to 8 carbons such as methoxy or n-hexoxy and the aryl moiety is phenyl, for example; —(CH$_2$)$_n$-aryl wherein said aryl is phenyl, for example; —(CH$_2$)$_n$-alkaryl wherein the alkyl moiety of said alkaryl is of alkyl about 1 to 8 carbons such as methyl or 2-methylpentyl and the aryl moiety is phenyl, for example; or —(CH$_2$)$_n$-alkoxyaryl wherein the alkoxy moiety of said alkoxyaryl is alkoxy of about 1 to 8 carbons such as methoxy or heptoxy and the aryl moiety is phenyl, for example. In each of the alkylphenyl and alkoxyphenyl moieties, the substitution on the phenyl is at the 2, 3 or 4 positions. Naphthyl is another possible aryl group or such moieties. A particular $R^3$ is —O—(CH$_2$)$_m$-alkaryl, wherein m is 0.

$R^4$, in more detail, is hydrogen or alkyl of about 1 to 4 carbons such as methyl, ethyl or t-butyl.

$R^5$, in more detail, is hydrogen or alkyl of about 1 to 2 carbons, such as methyl or ethyl.

$R^6$, in more detail, is hydrogen or alkyl of about 1 to 3 carbons such as methyl, ethyl, n-propyl or iso-propyl.

$R^7$, in more detail, is hydrogen or alkyl of about 1 to 3 carbons such as methyl, ethyl, n-propyl or iso-propyl.

k, in more detail, is the integer 2–7, particularly 3.

Specific compounds of the present invention are the following:
8-hydroxy-5-eicosynoic acid;
8-hydroxy-5(Z)-eicosenoic acid;

8-oxo-5(Z)-eicosenoic acid;
8-oxo-5-eicosynoic acid;
8-hydroxy-10-phenyl-5-decynoic acid;
8-hydroxy-10-phenyl-5(Z)-decenoic acid;
8-hydroxy-9-(4-pentylphenoxy)-5-nonynoic acid;
methyl 8-hydroxy-9-(4-pentylphenoxy)-5-nonynoate;
methyl 8-hydroxy-9-(4-pentylphenoxy)-5(Z)-nonenoate;
8-hydroxy-9-(4-pentylphenoxy-5(Z)-nonenoic acid;
methyl 8-(acetylthio)-9-(4-pentylphenoxy)-5(Z)-nonenoate;
8-mercapto-9-(4-pentylphenoxy)-5-nonynoic acid;
8-hydroxy-9-(4-pentylphenoxy)nonanoic acid; and
8-hydroxy-9-(4-pentylphenoxy)-5-nonynoic acid.

When Y is —COOH, the compounds of formula (I) of this invention may form salts with a physiologically acceptable base such as sodium or potassium hydroxide, carbonate or bicarbonate or an organic base such as tromethamine.

It is understood that compounds of formula (I) may exist in various isomeric forms, e.g. cis (Z)/trans (E) isomers formed in view of the presence of alkenyl groups as defined when A is —CR$^6$=CR$^7$—. The preferred configuration for —CR$^6$=CR$^7$— is cis. Optical isomers including diastereomers and individual enantiomers, racemates and other isomer ratios formed in view of the presence of one or more asymmetric carbon atoms in the compounds of formula (I) are also included within the scope of this invention.

The present invention includes all such cis/trans and optical isomers. In addition, compounds of formula (I) may exist as hydrated or solvated forms and the invention includes all such forms.

As used in the present specification, the terms "alkyl" and "alkoxy" includes all straight and branched chain alkyl and alkoxy groups within the carbon limits defined. The term "halo" includes fluorine, chlorine, bromine and iodine.

Compounds of formula (I) may be prepared by the following Reaction Scheme:

(II) H—A—(CH$_2$)$_k$—Y $\longrightarrow$ M—A—(CH$_2$)$_k$—Y (III)

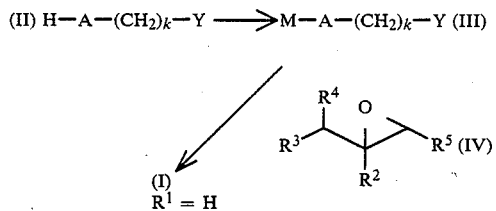

(I) R$^1$ = H

In the above Reaction Scheme, an acetylene compounds of formula (II) wherein A is —C≡C— is first converted to an acetylene salt of formula (III) wherein M is an alkali metal. The acetylene salt of formula (III) is then reacted with an epoxide of formula (IV) to produce a compound of formula (I) wherein A is —C≡C— and R$^1$ is OH. Compounds of formula (I) wherein A is —C≡C— and R$^1$ is OH may be further reacted to produce other members of formula (I) compounds.

In more detail, to produce compounds of formula (I) wherein A is —C≡C— and R$^1$ is OH, an acetylene compound of formula (II) is reacted with an alkali metal alkyl such as n-butyllithium in hexane, or with other metallation reagents such as potassium hydride, sodium hydride or ethyl magnesium bromide to produce an alkali metal acetylide of formula (II), wherein M is lithium, potassium, sodium or magnesium. When M is magnesium, obviously two anion moieties in the formula (III) compound would be required for each magnesium cation. The metallation reaction is conveniently carried out in a polar aprotic solvent such as hexamethylphosphoramide, THF, DMSO, or DMF at a temperature of about −30° C. to about 80° C., with about 9° C. being preferred. When anion formation is complete, the reaction mixture is treated with an epoxide of formula (IV) and allowed to stir at a temperature of about −30° C. to about 80° C., with about 25° C. preferred for a period of about one hour to about three days, with about 24 hours preferred. The reaction mixture is then acidified and the product is formula (I) wherein A is —C≡C— and R$^1$ is OH is obtained by conventional methods known to those skilled in the art of organic chemistry such as extraction, crystallization or chromatography.

To prepare compounds of formula (I) wherein A is cis —CR$^6$=CR$^7$—, and R$^6$ and R$^7$ are both hydrogen, the corresponding acetylene compound of formula (I) may be subjected to catalytic hydrogenation under Lindlar conditions in an ether-like solvent such as tetrahydrofuran in the presence of triethylamine or isoquinoline or over 5% Pd-BaSO$_4$ in a solvent such as pyridine under a hydrogen pressure of about 1 to 1.5 atm for a period of about 1 to 24 hours. Compounds of formula (I) wherein A is trans —CR$^6$=CR$^7$—, wherein R$^6$ and R$^7$ are both hydrogen, may be prepared by reduction of the corresponding acetylene compounds by treatment with lithium and liquid ammonia. To prepare compounds of formula (I), wherein A is —CH$_2$—, alkylidene or 1-alkylalkylidene, an acetylene compound of formula (I) is reacted under more vigorous Lindlar conditions than those described above for the preparation of the corresponding alkene compounds. Generally, a larger quantity of Lindlar's catalyst and longer hydrogenation times, i.e., exhaustive hydrogen uptake, are employed. Alternatively, a different catalyst may be employed such as PtO$_2$ or Pd/C at hydrogen pressures of about 1 to 4 atm.

To prepare compounds of formula (I) wherein Y is alkoxycarbonyl, an appropriate starting ester of formula (II) wherein Y is alkoxycarbonyl may be employed in the Reaction Scheme or, alternatively, the corresponding acid of formula (I) wherein Y is —COOH may be converted to the ester by conventional methods known in the art of organic synthesis, for example by Fisher esterification. Alternatively, an acid of formula (I) may be converted to a methyl ester by the action of diazomethane under standard conditions.

Compounds of formula (I) wherein Y is —CONH$_2$, N-alkylcarboxamido or N,N-dialkylcarboxamido may be prepared by employing the corresponding amides of formula (II) in the Reaction Scheme or, alternatively, may be prepared by reaction of the corresponding acid chloride of a formula (I) compound with ammonia or a primary alkyl amine or an N,N-dialkyl amine respectively. The acid chlorides may be prepared from the corresponding acid by treatment with thionyl chloride at a temperature of about 0° to 100° C. Obviously, the acid chloride route would not be preferred for the preparation of compounds of formula (I) wherein an unprotected active hydrogen is present, such as when R$^1$ is hydroxyl.

Compounds of formula (I) wherein R$^1$ is acetylthio may be prepared from the corresponding compound of formula (I) wherein R$^1$ is OH by reaction of the hydroxy compound with N-methyl-2-fluoropyridinium tosylate and thioacetic acid in the presence of triethylamine in a solvent such as toluene or a mixture of toluene and acetone. The reaction is conveniently carried out at room temperature to about the reflux temperature of the solvent. Conventional means are employed in the purification of the final products.

Compounds of formula (I) wherein $R^1$ is mercapto may be obtained from the corresponding acetylthio compounds under mild base hydrolysis conditions such as potassium carbonate in aqueous methanol at room temperature.

Formula (I) compounds wherein $R^1$ is alkylthio or alkoxy may be prepared by alkylation of the corresponding mercapto or hydroxy compounds respectively under normal alkylation conditions such as by treatment of an alkali metal salt of the mercapto or hydroxy compound with an appropriate alkyl halide in a polar aprotic solvent such as DMF or DMSO.

Formula (I) compounds wherein $R^1$ is chloro or bromo may be prepared by treatment of the corresponding compound of formula (I) wherein $R^1$ is hydroxyl with triphenyl phosphine and $CCl_4$ or $CBr_4$, thionyl chloride, $PCl_3$ or $PBr_3$. To prepare compounds of formula (I) wherein $R^1$ is iodo, the corresponding formula (I) compound where $R^1$ is hydroxy is first treated with methane sulfonyl chloride to form the corresponding mesylate. The mesylate is then reacted with an alkali metal iodide such as sodium or potassium iodide in a polar aprotic solvent such as DMF at a temperature of about 0°–50° C. to produce the formula (I) compound wherein $R^1$ is iodo. For formula (I) compounds where $R^1$ is fluoro, the corresponding $R^1$=OH compound may be reacted with $Et_2NSF_3$ as described by W. J. Middleton in the Journal of Organic Chemistry, Vol. 40, No. 5, pages 574–578 (1975); with $SeF_4$ as described by G. A. Olah in the Journal of the American Chemical Society, Vol. 96, pages 925–927 (1974); or with $SF_4$ as described in Organic Reactions, Vol. 21, John Wiley & Sons, pages 1–124 (1974).

Formula (I) compounds wherein $R^1$ and $R^2$ together is carbonyl may be prepared by oxidation of the corresponding hydroxy compounds with, for example, $CrO_3/H_2SO_4$ (Jones reagent) in a solvent such as acetone. Subsequent ketal formation of formula (I) compounds wherein $R^1$ and $R^2$ together is carbonyl will afford compounds of formula (I) wherein $R^1$ and $R^2$ together represents —$O(CH_2)_2O$— or —$O(CH_2)_3O$—. Ketal formation may be accomplished by methods known to those skilled in the art of organic chemistry such as treatment of the carbonyl compound with a diol of the formula $HO(CH_2)_pOH$, wherein p is 2 or 3, in the presence of a catalytic amount of p-toluenesulfonic acid.

The starting epoxides of formula (IV) may be obtained commercially or may be prepared from the corresponding alkene by standard epoxidation techniques known in the art such as treatment with m-chloroperbenzoic acid.

Starting compounds of formula (II) may be obtained commercially or prepared by methods known in the literature or analogous methods thereto. Particularly versatile formula (II) compounds are those wherein A is —C≡C— and Y is —COOH.

The compounds of formula (I) of this invention have been demonstrated to possess valuable antiallergic and anti-inflammatory properties by virtue of the following in vitro tests.

(a) Immunogically Mediated Contraction of the Parenchymal Strip (IMCPS)

This test demonstrates the effectiveness of an agent in preventing the contraction of guinea pig lung parenchymal tissue by blocking immunogical release of leukotriene products of the lipoxygenase pathway. It is a modification of the procedure published by K. Forsberg and L. Sorenby in Agents and Actions, Vol. 9 pp. 364–368 (1978). In this test, male Hartley strain guinea pigs weighting 400 to 600 g were sensitized by subcutaneous administration of chicken egg albumin (Sigma A-5503, 1.0 mg, 0.5% solution) and *bordetella pertussis*, $11 \times 10^9$ cells (Massachusetts Public health Biological Labs) 4 to 8 weeks prior to the experiment. The animals were sacrificed, the heart and lungs were removed en bloc and placed in Krebs solution at room temperature. Lung strips (2.5 cm in length) were cut from the perihperal edge of each lobe. Two strips were removed from each animal and were trimmed to be of equal length. Each strip was suspended in an isolated organ bath (10.0 ml) containing oxygenated Krebs buffer solution at 37.5° C. then attached to a force displacement transducer (Grass FTO3) and placed under an initial tension of 1.0 g. The tissues were allowed to equilibrate for 45–60 min, during which the bathing solution was changed several times. At the end of the equilbration period, chlorpheniramine (10.0μM) and indomethacin (100.0μM) were added to eliminate the contribution of histamine and prostaglandins to the contractile response. The two tissues from each animal were matched so that one tissue served as a control and the test drug dissolved in DMSO was added to the bath containing the other tissue at a final concentration of 100μM. After 30 min, egg albumin was added to each bath and the contractile response was measured as milligrams of tension developed as recorded on a Grass Model 7D polygraph. A test compound is considered active, if it demonstrates a 15% or greater inhibition in contraction of a guinea pig parenchymal strip, relative to the control tissue, at a drug concentration of 100μM.

(b) Human granulocyte Assay for Lipoxygenase Products (HGALP)

This test is a measurement of the inhibition of the synthesis or relase of [3H]-labeled lipoxygenase metabolites released or generated from human granulocyte cells that are prelabeled with [3H]-arachidonic acid. These metabolites include the leukotrienes (e.g., $LTB_4$) which are potent mediators of inflammation and allergy. In this test, a granulocyte enriched fraction is prepared from freshly drawn human blood (50 ml/donor) by standard techniques involving unit gravity separation on ficoll hypaque. Cells are prelabeled with [3H]-arachidonic acid (20 μCi in 2 ml cell suspension) during a 30 min incubation at 37° C. After washing out unincorporated label, the radiolabeled cells are brought up in incubation buffer (Minimum Essential Medium containing 14 μM indomethacin) to a $10^7$ cell/ml concentration. Cell suspensions (1 ml/sample) are preincubated for 5 min in the presence or absence of test drugs delivered in 5 μl dimethylsulfoxide (DMSO). Cell suspensions are challeged with 10 μM ionophore A23187 to activate the calcium-dependent metabolism of [3H-arachidonic acid.] after a 5 min incubation at 37° C., incubations are terminated by the addition of 1 ml ice cold phosphate buffered saline, and cells are pelleted by centrifugation. Supernatants are passed through C18 Sep Pak ® cartridges which are then washed twice with 1 ml water. Lipoxygenase metabolites are eluted with two 1 ml volumes of methanol. Eluates are collected in scintillation vials and counted in Aqueous Counting Scintillant (ACS). Radioactivity eluted with methanol is a measure of lipoxygenase metabolites. Values are normalized to vehicle (5 μl DMSO) treated controls and expressed as percent inhibition. Triplicate determinations at each drug concentration are analyzed as log-dose response curves by linear regression analysis from which IC$_{50}$ values are derived. The compounds of formula (I) of this invention are considered active in the HGALP test if they exhibit an inhibition or provide an estimate of potency in an IC$_{50}$ (concentration which produces at 50% inhibition).

The results of the IMCPS and the HGALP tests, employing the administration of various illustrative compounds of the present invention, are shown in Table I. The compounds are of the formula (I) wherein $R^1$, $R^2$, $R^3$, A and Y are as shown, $R^4$ and $R^5$ are hydrogen and k is 3.

TABLE I
Effect of Test Compounds in the IMCPS and HGALP Tests

| Compound of Ex. No. | $R^1$ | $R^2$ | $R^3$ | A | Y | IMCPS % Inhib @ 100 μM | HGALP IC$_{50}$ (μM) |
|---|---|---|---|---|---|---|---|
| 1d | OH | H | n-C$_{11}$H$_{23}$ | —C≡C— | —COOH | 20–43 | 12.0 |
| 2 | OH | H | n-C$_{11}$H$_{23}$ | —CH=CH— | —COOH | 19 | 7.5 |
| 3 | C=O | | n-C$_{11}$H$_{23}$ | —CH=CH— | —COOH | 24 | 13.0 |
| 4 | C=O | | n-C$_{11}$H$_{23}$ | —C≡C— | —COOH | 22 | 4.90 |
| 5 | OH | H | —CH$_2$Ph | —C≡C— | —COOH | 9–14 | 14.2 |
| 6 | OH | H | —CH$_2$Ph | —CH=CH— | —COOH | 9 | 13.0 |
| 7b | OH | H | —O—C$_6$H$_4$—C$_5$H$_{11}$ | —C≡C— | —COOH | 29 | 12.0 |
| 8 | OH | H | —O—C$_6$H$_4$—C$_5$H$_{11}$ | —C≡C— | —COOCH$_3$ | 14 | 8 |
| 9 | OH | H | —O—C$_6$H$_4$—C$_5$H$_{11}$ | —CH=CH— | —COOCH$_3$ | 0 | 14.0 |
| 10 | OH | H | —O—C$_6$H$_4$—C$_5$H$_{11}$ | —CH=CH— | —COOH | 28.5 | 1.1–9.5 |
| 11 | —S—CO—CH$_3$ | H | —O—C$_6$H$_4$—C$_5$H$_{11}$ | —CH=CH— | —COOCH$_3$ | 3 | 8.5 |
| 12b | SH | H | —O—C$_6$H$_4$—C$_5$H$_{11}$ | —C≡C— | —COOH | 29 | 13.0 |
| 13* | OH | H | —O—C$_6$H$_4$—C$_5$H$_{11}$ | —CH$_2$— | —COOH | 6 | 2.3 |
| 14b | OH | H | —O—C$_6$H$_4$—OC$_5$H$_{11}$ | —C≡C— | —COOH | 0–30 | 33.0 |

*k = 4

Also part of the present invention are pharmaceutical composition and methods, e.g. for the treatment of allergic reactions and inflammatory disorders using such compositions. To prepare the pharmaceutical compositions of this invention, one or more compounds or salts thereof of the invention as the active ingredient, is intimately admixed with a pharmaceutical carrier according to conventional pharmaceutical compounding techniques. One particular route of administration would employ administration of the active compound of formula (I) by means of an inhalation device. An example is a turboinhaler such as the Spinhaler® device produced by Fisons Corp. of Bedford, Mass. for Intal ® brand of cromolyn sodium. In this system, a compound of formula (I) may be micronized together with a lactose carrier and inhaled with the use of the Spinhaler. Alternatively, the active compound may be made into a nebulizer water solution or suspension and used as mist after being nebulized with an appropriate air nebulizer in a manner similar to that used with Intal ® brand of cromolyn sodium. Another inhaler device which can be used for the compounds of formula (I) is the Beclovent ® inhaler obtained from Glaxo, Inc. of Research Triangle Park, NC. In this system, a suspension of the active ingredient in propellants such as trichloromonofluoromethane or dichlorodifluoromethane and oleic acid is provided and each activation of the inhaler cannister delivers a metered dose to be inhaled by the patient having allergic symptoms.

The pharmaceutical inhalation compositions herein will contain per dosage unit from about 0.01 to about 10.0 mg of the active ingredient, and, preferably, from about 0.01 to about 1.0 mg.

Alternate routes of administration of the compounds of formula (I) of this invention may be by injection, either subcutaneously or intraveneously. When administered by the subcutaneous route, the dosage unit will contain from about 0.1 to 100 mg of the active ingredient, and, preferably, from about 0.1 to 1.0 mg. When administered by the intraveneous route, the dosage unit will contain from about 0.1 to 20 mg of the active ingredient, and preferably, from about 0.1 to 1.0 mg.

In the following examples and throughout the specification, the following abbreviations may be used: mg (milligrams); g (grams); kg (kilograms); ml (milliliters); mmole (millimoles); µM (micromolar); mM (millimolar); M (molar); N (normal); psi (pounds per square inch); mp (melting point); bp (boiling point); meq (milliequivalents); E (trans); Z (cis); RT (room temperature); Et (ethyl); $Et_2O$ (diethyl ether); EtOAc (ethyl acetate); MeOH (methanol); EtOH (ethanol); i-PrOH (isopropanol); LAH (lithium aluminum hydride); THF (tetrahydrofuran); DMF (dimethylformamide); DMSO (dimethylsulfoxide); HMPA (hexamethyl phosphoramide); hr (hours); min (minutes); atm (atmospheres of pressure); s.c. (subcutaneous); i.v. (intravenous); and C, H, N, O etc. (the chemical symbols for the elements). Unless otherwise indicated, all temperatures are reported in °C. (degress centigrade).

The following examples are intended to describe the preparation of various compounds of formula (I) of this invention. They are to be considered representative of the chemistry employed, but not to be considered limiting as to the scope or to kind.

EXAMPLE 1 a. 5-Cyanopentyne

A mixture of 102.5 g (1 mole) of 5-chloropentyne, 143 g (2.2 moles) of potassium cyanide, 1.4 liters of EtOH and 280 ml of water was refluxed 12 hr. Ethanol was removed and the residue was extracted with $Et_2O$ twice. The organic layers were combined and washed with water and then dried over $Na_2SO_4$. The residue, after removal of solvent, was distilled through a vigreux column to obtain the title compound, bp 75°–80° /15 mmHg, as a colorless liquid.

b. 5-Hexanoic Acid

A mixture of 43 g (0.46 mole) of 5-cyanopentyne, the product of Example of 1a, and 300 ml of 10% aqueous NaOH was heated at 90° C. for 7 hr. The reaction solution was cooled to 5°–10° and then acidified with 12N HCl. The aqueous solution was extracted with $Et_2O$ three times. The extractant was washed with saturated NaCl solution and dried over $MgSO_4$. The residue, after removal of solvent, was distilled to give title compound, bp 75°–78°/0.02 mm Hg.

c. Dodecyl Oxirane

In a flask equipped with a mechanical stirrer and an addition funnel was placed 19.8 g (0.1 mole) of 1-tetradecene and 150 ml of $CH_2Cl_2$. The solution was stirred and a suspension of 23 g (0.106 mole) of m-chloroperbenzoic acid in 250 ml of $CH_2Cl_2$ was added dropwise. After stirring overnight, the $CH_2Cl_2$ solution was washed with 10% aqueous $NaHSO_3$, saturated $NaHCO_3$ solution and then dried over $Na_2SO_4$. The residue, after removal of solvent, was distilled through a vigreux column to obtain the title compound, bp 78°–81°/0.01 mmHg as a colorless liquid.

d. 8-Hydroxy-5-eicosynoic acid

In a dry flask under argon was placed 10.2 g of 5-hexynoic acid, the product of 1b, and 100 ml of HMPA (distilled over NaH). The solution was cooled to 0° C. and a solution of n-BuLi in hexane (115 ml, 0.185 mol) was added dropwise. After stirring for 1 hr., 21.7 g (0.118 mole) of dodecyl oxirane, the product of 1 c, was added dropwise. The reaction mixture was allowed to stir at room temperature for 3 days and then poured into 150 ml of ice and water. The aqueous solution was acidified with 5% HCl and then extracted with ether. The ether solution was washed with $H_2O$, saturated with NaCl solution and then dried over $MgSO_4$. Removal of solvent yielded crude product which was recrystallized in cyclohexane to give the title compound, mp 80.5°–81°.

Elemental Analysis: Calculated for $C_{20}H_{36}O_3$: C, 74.03; H, 11.18. Found: C, 73.84; H, 11.01.

EXAMPLE 2

8-Hydroxy-5(Z)-eicosenoic Acid

A mixture of 3.7 g of 8-hydroxy-5-eicosynoic acid, the product of Example 1d, and 110 mg of Lindlar's catalyst in 2.5 ml of $Et_3N$ and 80 ml THF was hydrogenated under 1 atm of hydrogen for 6 hr. The catalyst was removed by filtration and solvent was removed. The residue was dissolved in 150 ml ether and washed with 5% HCl, NaCl solution and then dried over $MgSO_4$. The crude product after removal of solvent was triturated with petroleum ether (bp 65°–90°) to yield the title compound, mp 43°–45°.

Elemental Analysis: Calculated for $C_{20}H_{38}O_3$: C, 73,58; H, 11.73. Found: C, 72.95; H, 11.84.

EXAMPLE 3

8-oxo-5-(Z)-eicosenoic Acid

To a solution of 1.88 g of 8-hydroxy-5(Z)-eicosenoic acid, the product of Example 2, in 50 ml of acetone with vigorous stirring at 5° was added 1.75 ml of Jones reagent (3.67M). The reaction mixture was stirred for 30 min and 100 ml of ether was added and then was washed with $H_2O$, dried over $MgSO_4$. Solvent was removed and the residue was recrystallized in petroleum ether to yield the title compound, mp 40.5°–51°.

Elemental Analysis: Calculated for $C_{20}H_{36}O_3$: C, 74.03; H, 11.18. Found: C, 73.54; H, 11.05.

EXAMPLE 4

8-Oxo-5-eicosynoic Acid

A solution of 4.22 g of 8-hydroxy-5-eicosynoic acid, the product of Example 1d, in 200 ml of acetone with vigorous stirring at 5° was added 5.5 ml of Jone's reagent (2.67M). The reaction mixture was stirred for 30 min and then 700 ml of Et$_2$O and 2 ml of MeOH was added and stirred for additional 3 min. The resulting reaction mixture was washed with H$_2$O, saturated NaCl solution and dried over MgSO$_4$. The crude product after removal of solvent was recrystallized in cyclohexane to yield the title compound, mp 79°–80.5°.

Elemental Analysis: Calculated for C$_{20}$H$_{34}$O$_3$: C, 74.48; H, 10.63. Found: C, 74.40; H, 10.66.

EXAMPLE 5

8-Hydroxy-10-phenyl-5-decynoic Acid Hydrate (10:1)

In a dry flask under N$_2$ was placed 200 ml of HMPA (distilled over NaH) and 24.4 g (0.218 mole) of 5-hexynoic acid, the product of 1b. The solution was stirred at 0° and was added a solution of n-BuLi in hexane (256 ml, 0.436 mole) dropwise. After 2 hours stirring, 2-phenylethyloxirane (33.9 g. 0.229 mole) was added and stirring was continued at RT for 2 days. The reaction mixture was cooled to 0° and 200 ml of H$_2$O was added. The aqueous solution was acidified with 6N HCl and then extracted with Et$_2$O three times. The ether solution was washed once with H$_2$O and was extracted with aqueous NH$_4$OH solution. The aqueous NH$_4$OH solution was reacidified with 6N HCl and then extracted with ether. Removal of the solvent yielded the crude product. The crude product was converted to the corresponding methyl ester via reaction with MeOH in the presence a catalytic amount of BH$_3$·Et$_2$O (0.2 ml). The methyl ester was purified by flash column chromatography (Silica gel, EtOAc-petroleum ether(1:4)) and subsequently was hydrolyzed to the acid in the mixture of K$_2$CO$_3$-MeOH-H$_2$O at RT. The acid was distilled through a Kugelrohr adaptor to give the title compound, bp 190°–195°/0.01 nmmHg (pot temperature).

Elemental Analysis: Calculated for C$_{16}$H$_{20}$O$_3$·0.1 H$_2$O: C,73.31; H,7.69. Found: C,73.74; H,7.77; H$_2$O, 0.75%.

EXAMPLE 6

8-Hydroxy-10-phenyl-5(Z)-decenoic Acid

A mixture of 5.8 g of the methyl ester of 8-hydroxy-10-phenyl-5-decynoic acid, prepared in Example 5, 50 ml of pyridine and 90 mg of 5% Pd on BaSO$_4$ was hydrogenated under 1 atm of hydrogen until the uptake of hydrogen ceased. The catalysts and solvent were removed and the residue was dissolved in ethyl ether and was washed with 5% HCl, NaHCO$_3$ solution and saturated NaCl solution. Removal of the solvent obtained an oil which was subsequently stirred in a mixture of 5.4 g of K$_2$CO$_3$, 50 ml of MeOH and 20 ml of H$_2$O for 2 days at RT. The MeOH was removed and the aqueous solution was acidified with 6N HCl and then extracted with Et$_2$O. Removal of solvent yielded the title compound.

Elemental Analysis: Calculated for C$_{16}$H$_{22}$O$_3$: C, 73.25; H, 8.45. Found: C, 73.07; H, 8.52.

EXAMPLE 7 a. 2-(4-Pentylphenoxymethyl)oxirane

A mixture of 44 g of 4-pentylphenol (Eastman Kodak), 50 ml of epichlolorohydrin, 120 g of potassium carbonate in 250 ml methyl ethyl ketone was refluxed for 12 hr. Residual after removal of solid and solvent was distilled through a Kugelrohr adaptor to give the title compound, bp 180°–195°/0.3 mmHg.

b. 8-Hydroxy-9(4-pentylphenoxy)-5-nonynoic acid

In a dry flask under N$_2$ was placed 150 ml of HMPA (distilled over NaH) and 15.61 g (0.14 mole) of 5-hexynoic acid, the product of Example 1b, and the mixture cooled in an ice-water bath. A solution of 190 ml of n-BuLi in hexane (0.295 mole) was added dropwise into the flask with stirring. Stirring was continued for an additional 2 hr and 37 g of 2-(4-pentylphenoxymethyl)oxirane, the product of Example 7a, was added. After 2 days stirring, the resulting reaction mixture was poured into an ice water mixture and acidified with 3N HCl. The aqueous solution was extracted with Et$_2$O three times. The organic layers were combined and then washed with aqueous 3N NH$_4$OH. The NH$_4$OH solution was acidified with 3N HCl and was extracted with Et$_2$O. The ether solution was dried over MgSO$_4$ and solvent removed to give an oil. The oil was purified by silical gel column chromatography (CHCl$_3$-MeOH) and then recrystallized in petroleum ether-EtOAc to give the title compound, mp 54°–57° C.

Elemental Analysis: Calculated for C$_{20}$H$_{28}$O$_4$: C, 72.26; H, 8.49. Found: C, 72.26; H, 8.52.

EXAMPLE 8

Methyl 8-Hydroxy-9-(4-pentylphenoxy)-5-nonynoate

A solution of 3 g of 8-hydroxy-9-(4-pentylphenoxy)-5-nonynoic acid, the product of Example 7b, 40 ml of MeOH, 40 ml of toluene and 3 drops of BF$_3$·Et$_2$O was heated for 12 hr to reflux with a Dean Stark trap to remove water. Solvent was removed and the residue was dissolved in Et$_2$O and was washed NaHCO$_3$ solution and NaCl solution. The ether solution was dried over MgSO$_4$ and removed solvent to give the title compound, an oil.

Calculated for C$_{21}$H$_{30}$O$_4$: C, 72.80; H, 8.73. Found: C, 72.58; H, 8.79.

EXAMPLE 9

Methyl 8-Hydroxy-9-(4-pentylphenoxy)-5(Z)-nonenoate

A mixture of 3.27 g of methyl 8-hydroxy-9-(4-pentylphenoxy)-5-nonynoate, the product of Example 8, 0.15 g of 5% Pd on BaSO$_4$ and 50 ml of pyridine was hydrogenated under 1 atm of hydrogen gas until the uptake hydrogen cased. The solvent and catalyst were removed and the residue was dissolved in Et$_2$O, washed with 1N HCl and with NaHCO$_3$ and then dried over MgSO$_4$. The residue, after removal of solvent, was purified by silica gel column chromatography (petroleum ether-EtOAc 5:1) to give the title compound.

Elemental Analysis: Calculated for C$_{21}$H$_{32}$O$_4$: C, 72.38; H, 9.25. Found: C, 72.37; H, 9.28.

EXAMPLE 10

8-Hydroxy-9-(4-pentylphenoxy)-5-(Z)-nonenoic acid

A mixture of 12.69 g of 8-hydroxy-9-(4-pentylphenoxy)-5-nonynoic acid, the product of Example 7b, 100 mg of 5% Pd on BaSO$_4$ and 100 ml of pyridine was hydrogenated under 1 atm of hydrogen gas until the uptake of hydrogen ceased. The catalyst and solvent were removed and the residue was distilled through a Kugelrohr adaptor to yield the title compound, bp 210°–220°/0.02 mmHg. The product was further purified by a silical gel column (CHCl$_3$-MeOH, 100:1).

Elemental Analysis: Calculated for C$_{20}$H$_{30}$O$_4$: C, 71.82; H, 9.04. Found: C, 71.30; H, 9.09.

EXAMPLE 11

Methyl 8-(Acetylthio)-9-(4-pentylphenoxy)-5-(Z)-nonenoate

In a dry flask equipped with a condenser was placed 1.42 g of methyl 8-hydroxy-9-(4-pentylphenoxy)-5-(Z)-nonenoate, the product of Example 9, 0.61 ml of Et$_3$N, 16 ml of toluene and 16 ml of acetone. To the mixture was added 1.25 g of N-methyl-2-fluoropyridinium tosylate (prepared according to the procedure of C. S. Marvel et al., J. Amer. Chem. Soc., 51, 3638 (1929)). Stirring at RT for 1 hr, a solution of 0.31 ml of thioacetic acid and 0.61 ml of Et$_3$N in 20 ml of toluene was added. The resulting reaction solution was refluxed for 2 hr. The solvent was removed and the residue was dissolved in EtOAc and was washed with NaHCO$_3$ solution. The residue, after removal of solvent, was purified by silical gel column chromatography (EtOAc-hexane) to give the title compound.

Elemental Analysis: Calculated for C$_{23}$H$_{34}$O$_4$S: C, 67.95; H, 8.29; S, 7.86. Found: C, 67.99; H, 8.47; S, 7.90.

EXAMPLE 12 a. Methyl 8-(Acetylthio)-9-(4-pentylphenoxy)-5-nonynoate

In a dry flask equipped with a condenser was placed 4 g of methyl 8-hydroxy-9-(4-pentylphenoxy)-5-nonynoate, the product of Example 8, 1.69 ml of Et$_3$N, 20 ml of toluene and 20 ml of acetone. To the mixture was added 3.43 g of N-methyl-2-fluoropyridimium tosylate stirring at RT for 1 hr. A solution of 0.87 ml of thioacetic acid and 1.69 ml of Et$_3$N in 5 ml of toluene was added. The resulting solution was refluxed for 2 hr. Solvent was removed and the residue was dissolved in Et$_2$O and then was washed with NaHCO$_3$ solution and dried over MgSO$_4$. The crude product, after solvent removal, was purified on a Waters Prep 500 HPLC (EtOAc-hexane 1:16) to obtain the title compound.

b. 8-Mercapto-9-(4-pentylphenoxy)-5-nonynoic acid

A mixture of 0.73 g of methyl 8-(acetylthio)-9-(4-pentylphenoxy)-5-nonynoate, the product of Example 12a, 1.25 g of potassium carbonate, 0.6 ml of H$_2$O and 32 ml of MeOH was stirred at RT for 12 hr. MeOH was removed and the residue was acidified with 3N HCL and extracted with Et$_2$O to obtain the crude product. The crude product was purified by silical gel chromatography (CH$_2$Cl$_2$-MeOH) and then recrystallized in petroleum ether-Et$_2$O to obtain the title compound, mp 70.0–70.5.

Elemental Analysis: Calculated for C$_{20}$H$_{28}$O$_3$S: C, 68.93; H, 8.10, S, 9.20. Found: C, 68.90; H, 8.12; S, 9.25.

EXAMPLE 13

8-Hydroxy-9-(4-pentylphenoxy)nonanoic Acid

A mixture of 3.5 g of 8-hydroxy-9-(4-pentylphenoxy)-5-nonynoic acid, 0.3 g of Lindlar's catalyst, 2.5 ml of Et$_3$N and 80 ml of THF was hydrogenated under 1 atm of hydrogen until the uptake hydrogen ceased. The solvent and catalyst were removed. The crude product was recrystallized in toluene to yield the title compound, mp 105.0°–105.5°. CI-MS (high resolution) (M+1=337.2298).

EXAMPLE 14 a. 2-(4-pentoxyphenoxymethyl)oxirane

A mixture of 24.41 g of 4-pentoxyphenol, 56 g of K$_2$CO$_3$, 34.7 ml of epicholorohydrin and 500 ml of methyl ethyl ketone was refluxed overnight. Solvent and solid were removed to yield a residue which was distilled by a Kugelrohr adaptor to give the title compound, bp 175°/0.01 mmHg.

b. 8-Hydroxy-9-(4-pentoxyphenoxy)-5-nonynoic acid

A dry flask equipped with an addition funnel and a mechanical stirrer under Ar was charged with 100 ml of HMPA and 9.7 g of 5-hexynoic acid. The flask was cooled in an ice water bath and a solution of n-BuLi in hexane (118 ml, 0.189 mole) was added dropwise. The resulting reaction mixture was stirred for 1.5 hr and then a solution of 24.5 g of 2-(4-pentoxyphenoxymethyl)oxirane, the product of Example 14a, in 20 ml of HMPA was added and stirring was continued for 2 days. The reaction mixture was poured into water and extracted with Et$_2$O three times. The ether solution was washed with aqueous NH$_4$OH twice. The aqueous solution was acidified with HCl and extracted with Et$_2$O. The ether solution was washed with saturated NaCl solution, dried over MgSO$_4$. Solvent was removed to give the crude product which was recrystallized in cyclohexane to give the title compound, mp 58.0°–60.0°.

Elemental Analysis: Calculated for C$_{20}$H$_{28}$O$_5$: C, 68.94; H, 8.10. Found: C, 69.01; H, 8.00.

What is claimed is:

1. A method for the treatment of allergic reactions or inflammatory disorders in a mammal which comprises administering to the mammal a pharmaceutical composition which comprises a combination of a pharmaceutically-acceptable diluent or carrier and a fatty acid compound of the following formula (I):

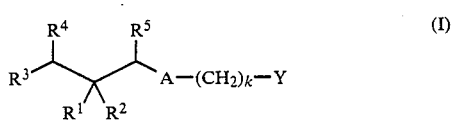

wherein

A is —CH$_2$—, alkylidene, 1-alkylalkylidene, —CR$^6$=CR$^7$—, or —C≡C—;

Y is —COOH, alkoxycarbonyl, —CONH$_2$, —CONHOH, N-alkylcarboxamido or N,N-dialkylcarboxamido;

R$^1$ is hydroxy, mercapto, acetoxy, acetylthio, alkoxy, alkylthio or halo;

R$^2$ is hydrogen or R$^1$ and R$^2$ taken together are carbonyl, —O(CH$_2$)$_2$O— or —O(CH$_2$)$_3$O—;

R$^3$ is alkyl, alkoxy, —O—(CH$_2$)$_m$—alkaryl, —O—(CH$_2$)$_m$—alkoxyaryl, —(CH$_2$)$_n$—aryl, —(CH$_2$)$_n$—alkaryl or —(CH$_2$)$_n$—alkoxyaryl;

R$^4$ is hydrogen or alkyl;

R$^5$ is hydrogen or alkyl;

R$^6$ is hydrogen or alkyl;

R$^7$ is hydrogen or alkyl;

k is the integer 2–7;

m is the integer 0–4;

n is the integer 1–6; and when Y is —COOH, the pharmaceutically-acceptable base addition salts thereof.

2. The method of claim 1, wherein $R^3$ is alkyl of at least 6 carbons.

3. The method of claim 1, wherein A is —CH$_2$—, alkylidene, 1-alkylalkylidene, —CR$^6$=CR$^7$— or —C≡C—;
Y is —COOH, alkoxycarbonyl wherein the alkoxy moiety is of about 1 to 4 carbons, —CONH$_2$, —CONHOH, N-alkylcarboxamido wherein the alkyl is of about 1 to 4 carbons or N,N-dialkylcarboxamido wherein the alkyl groups are independently of about 1 to 4 carbons each;
$R^1$ is hydroxy, mercapto, acetoxy, acetylthio, alkoxy of about 1 to 4 carbons, alkylthio of about 1 to 4 carbons, fluoro, chloro, bromo or iodo;
$R^2$ is hydrogen or $R^1$ and $R^2$ taken together are carbonyl, —O(CH$_2$)$_2$O— or —O(CH$_2$)$_3$O—;
$R^3$ is alkyl of about 6 to 15 carbons, alkoxy of about 6 to 15 carbons, —O—(CH$_2$)$_m$—alkaryl wherein the alkyl moiety is of about 1 to 8 carbons and the aryl is phenyl, —O—(CH$_2$)$_m$—alkoxyaryl wherein the alkoxy moiety is of about 1 to 8 carbons and the aryl is phenyl, —(CH$_2$)$_n$—aryl wherein said aryl is phenyl, —(CH$_2$)$_n$—alkaryl wherein the alkyl moiety is of about 1 to 8 carbons and the aryl is phenyl, or —(CH$_2$)$_n$—alkoxyaryl wherein the alkoxy moiety is of about 1 to 8 carbons and the aryl moiety is phenyl;
$R^4$ is hydrogen or alkyl of about 1 to 4 carbons;
$R^5$ is hydrogen or alkyl of about 1 to 2 carbons;
$R^6$ is hydrogen or alkyl of about 1 to 3 carbons;
$R^7$ is hydrogen or alkyl of about 1 to 3 carbons;
k is the integer 2–7;
m is the integer 0–4; and
n is the integer 1–6.

4. The method of claim 1, wherein Y is —COOH.

5. The method of claim 1, wherein A is —CR$^6$=CR$^7$—.

6. The method of claim 5, wherein $R^6$ and $R^7$ are both hydrogen.

7. The method of claim 5, wherein A is the cis-isomer.

8. The method of claim 5, wherein A is the trans-isomer.

9. The method of claim 1, wherein $R^1$ is hydroxy.

10. The method of claim 1, wherein $R^1$ together with $R^2$ are carbonyl.

11. The method of claim 1, wherein $R^3$ is —O—(CH$_2$)$_m$-alkaryl.

12. The method of claim 1, wherein k is the integer 3.

13. The method of claim 1, wherein said fatty acid compound is selected from the group consisting of:
8-hydroxy-5-eicosynoic acid;
8-hydroxy-5-eicosenoic acid;
8-oxo-5-eicosenoic acid;
8-oxo-5-eicosynoic acid;
6-hydroxy-10-phenyl-5-decynoic acid;
8-hydroxy-10-phenyl-5-decenoic acid;
8-hydroxy-9-(4-pentylphenoxy)-5-nonynoic acid;
methyl 8-hydroxy-9-(4-pentylphenoxy)-5-nonynoate;
methyl 8-hydroxy-9-(4-pentylphenoxy)-5-nonenoate;
8-hydroxy-9-(4-pentylphenoxy)-5-nonenoic acid;
methyl 8-(acetylthio)-9-(4-pentylphenoxy)-5-nonenoate;
8-mercapto-9-(4-pentylphenoxy)-5-nonynoic acid;
8-hydroxy-9-(4-pentylphenoxy)nonanoic acid; and
8-hydroxy-9-(4-pentylphenoxy)-5-nonynoic acid.

14. The method of claim 1, wherein said fatty acid is 8-hydroxy-9-(4-pentylphenoxy)-5-(Z)-nonenoic acid.

15. The method of claim 1, wherein said method is for the treatment of allergic reactions in a mammal.

16. The method of claim 1, wherein said method is for the treatment of inflammatory disorders in a mammal.

17. The method of claim 1, wherein $R^3$ is alkoxy.

18. The method of claim 19, wherein $R^3$ is —O—(CH$_2$)$_m$—alkoxyaryl.

19. The method of claim 1, wherein $R^3$ is —(CH$_2$)$_n$—aryl.

20. The method of claim 1, wherein $R^3$ is —(CH$_2$)$_n$—alkoxyaryl.

* * * * *

UNITED STATES PATENT AND TRADEMARK OFFICE
CERTIFICATE OF CORRECTION

PATENT NO. : 4,908,384

DATED : Mar. 13, 1990

INVENTOR(S) : Ho et al.

It is certified that error appears in the above-identified patent and that said Letters Patent is hereby corrected as shown below:

Claim 18, Column 16, Line 34

"The method of claim 19,"

Should be:

"The method of claim 1,"

Signed and Sealed this

Twenty-eighth Day of May, 1991

*Attest:*

HARRY F. MANBECK, JR.

*Attesting Officer*   *Commissioner of Patents and Trademarks*